(12) United States Patent
    Grill

(10) Patent No.:     US 12,605,670 B2
(45) Date of Patent:        Apr. 21, 2026

(54) BIOGAS HALOGENATED VOLATILE ORGANIC COMPOUND AND ACID REMOVAL SYSTEMS AND METHODS

(71) Applicant: Stearns, Conrad and Schmidt, Consulting Engineers, Inc., Reston, VA (US)

(72) Inventor: Jeffrey Grill, Cypress, CA (US)

(73) Assignee: Stearns, Conrad and Schmidt, Consulting Engineers, Inc., Reston, VA (US)

( * ) Notice: Subject to any disclaimer, the term of this patent is extended or adjusted under 35 U.S.C. 154(b) by 0 days.

(21) Appl. No.: 18/169,377

(22) Filed: Feb. 15, 2023

(65) Prior Publication Data

US 2024/0269602 A1     Aug. 15, 2024

(51) Int. Cl.
    B01D 53/04      (2006.01)
    B01D 53/26      (2006.01)
    B01D 53/40      (2006.01)
    B01D 53/75      (2006.01)
    B01D 53/82      (2006.01)
    C07C 7/12      (2006.01)

(52) U.S. Cl.
    CPC .......... B01D 53/04 (2013.01); B01D 53/265 (2013.01); B01D 53/40 (2013.01); B01D 53/82 (2013.01); C07C 7/12 (2013.01); *B01D 2253/304* (2013.01); *B01D 2257/206* (2013.01); *B01D 2257/708* (2013.01); *B01D 2257/80* (2013.01)

(58) Field of Classification Search
    CPC ...... B01D 53/04; B01D 53/265; B01D 53/40; B01D 53/82; B01D 2253/304; B01D 2257/206; B01D 2257/708; B01D 2257/80; C07C 7/12
    See application file for complete search history.

(56) References Cited

U.S. PATENT DOCUMENTS

| | | | | |
|---|---|---|---|---|
| 5,846,295 A | * | 12/1998 | Kalbassi | F25J 3/04157 |
| | | | | 95/123 |
| 8,211,211 B1 | * | 7/2012 | Knaebel | B01D 53/75 |
| | | | | 95/122 |
| 9,217,116 B2 | * | 12/2015 | Huang | C10L 3/102 |
| 2003/0159994 A1 | * | 8/2003 | Blachman | B01J 20/28004 |
| | | | | 210/660 |
| 2007/0068386 A1 | * | 3/2007 | Mitariten | B01D 53/04 |
| | | | | 95/116 |
| 2014/0058118 A1 | * | 2/2014 | Rende | B01J 12/005 |
| | | | | 564/204 |
| 2021/0402368 A1 | * | 12/2021 | Baek | C10K 1/143 |

* cited by examiner

*Primary Examiner* — In Suk C Bullock
*Assistant Examiner* — Jason Y Chong
(74) *Attorney, Agent, or Firm* — Maier & Maier, PLLC

(57)        ABSTRACT

A method to produce an acid-depleted biogas is described. The method includes supplying biogas to a biogas acid removal system to produce an acid-depleted biogas. Biogas pre-processing, post-processing, and a product production system may be integrated with the biogas acid removal process to produce a product. A two-stage volatile organic compound removal process is also described including a volatile organic compound removal step, and a halogenated volatile organic compound removal step, followed by an acid removal step. Oxygen removal from the biogas is also provided by combusting oxygen together with halogenated volatile organic compounds within the biogas, followed by removing acid generated in the combustion of the halogenated volatile organic compounds.

19 Claims, 5 Drawing Sheets

PRODUCT PRODUCTION SYSTEM

BIOGAS ACID REMOVAL SYSTEM

BIOGAS ACID REMOVAL SYSTEM

BIOGAS ACID REMOVAL SYSTEM

PRODUCT PRODUCTION SYSTEM

TWO-STAGE
VOLATILE ORGANIC COMPOUND
REMOVAL PROCESS

BIOGAS HALOGENATED VOLATILE ORGANIC COMPOUND AND ACID REMOVAL SYSTEMS AND METHODS

TECHNICAL FIELD

The present disclosure relates to improvements to processing of biogas and production of biogas-related products.

BACKGROUND

Biogas is produced by the biological breakdown of organic matter. Methane is an important constituent of biogas which may be processed to produce a variety of valuable products. However, some biogas sources include problematic contaminants such as an acid and additionally some sources of biogas include halogenated volatile organic compounds which could be prone to having the halogen disassociate therefrom and become an acid.

An acid within a source of biogas can cause problems to owners and operators of biogas processing facilities. For example, the acid within biogas can cause corrosion of metal components within biogas processing equipment and can result in added replacement and unexpected repair costs in the facility. As a result, replacement of corroded equipment within the biogas processing system can result in lost profits due to plant down time while not producing a sellable product. Further, and most important, corrosion of biogas processing equipment and piping can lead to safety issues, for example, asset failure, such as a ruptured equipment item or pipe in a pressurized environment can result in plant personnel being exposed to less than desirable working conditions.

Further, it is of importance to owners and operators of biogas processing facilities to adhere to stringent quality control measures to deliver a high-quality, predictable product to the end-user, that is not contaminated with an acid which may cause further problems for the utility or consumer.

There exists a need to remove halogenated volatile organic compounds from a source of biogas. There also exists a need to first remove halogenated volatile organic compounds from a source of biogas and then subsequent acids generated from the pre-processing the biogas comprising the halogenated volatile organic compounds.

Therefore, a need exists to reliably produce a biogas-related product that has undergone an acid removal process to maintain consistent and safe operations of the biogas processing facility, while protecting assets to avoid and reduce additional costs, to produce a safe and on-specification biogas-related product to the utility and/or consumer.

SUMMARY

This Summary is provided merely to introduce certain concepts and not to identify any key or essential features of the claimed subject matter.

In embodiments, the method to produce an acid-depleted biogas, comprises:

providing an acid-laden biogas comprising an acid;
  providing a biogas acid removal system comprising an acid removal material, said biogas acid removal system is configured to accept said acid-laden biogas and to contact said acid-laden biogas with said acid removal material within said biogas acid removal system to remove at least a portion of said acid within said acid-laden biogas to produce said acid-depleted biogas, said acid-depleted biogas comprises a reduced amount of said acid relative to said acid-laden biogas; wherein said biogas acid removal system does not comprise a liquid caustic scrubber; and
  supplying said acid-laden biogas to said biogas acid removal system, wherein within said biogas acid removal system said acid-laden biogas is contacted with said acid removal material to remove said at least a portion of said acid from said acid-laden biogas to produce said acid-depleted biogas, wherein said acid-depleted biogas comprises a reduced amount of said acid relative to said acid-laden biogas.

In embodiments, said biogas acid removal system comprises a vessel, wherein said vessel comprises an interior with said acid removal material positioned within said interior; and said method further comprises supplying said acid-laden biogas to said vessel, wherein said acid-laden biogas contacts said acid removal material positioned within said interior of said vessel to produce said acid-depleted biogas.

In embodiments, said biogas acid removal system comprises a plurality of vessels, wherein each of said plurality of vessels comprise an interior with said acid removal material positioned within said interior; said plurality of vessels comprises a first vessel and a second vessel; said first vessel is configured to accept said biogas and to remove a first portion of said acid therefrom to produce an intermediate acid-depleted biogas by contacting said biogas with said acid removal material within said first vessel; said second vessel is configured to accept said intermediate acid-depleted biogas from said first vessel and to remove a second portion of said acid therefrom to produce said acid-depleted biogas by contacting said intermediate acid-depleted biogas with said acid removal material included within said second vessel; and said method further comprises:

supplying said acid-laden biogas to said first vessel to remove said first portion of said acid therefrom to produce said intermediate acid-depleted biogas by contacting said acid-laden biogas with said acid removal material within said first vessel; and
  supplying said intermediate acid-depleted biogas from said first vessel to said second vessel to remove said second portion of said acid therefrom to produce said acid-depleted biogas by contacting said intermediate acid-depleted biogas with said acid removal material included within said second vessel;
  wherein:
  said intermediate acid-depleted biogas comprises a reduced amount of acid relative to said acid-laden biogas; and
  said acid-depleted biogas comprises a reduced amount of acid relative to said intermediate acid-depleted biogas.

In embodiments, said acid removal material within said second vessel comprises a type of acid removal material different from said acid removal material within said first vessel.

In embodiments, said acid-laden biogas is a pre-processed biogas; and said method further comprises:

providing a pre-processing system configured to accept a source of biogas and to process said source of biogas to produce a pre-processed biogas;
  supplying a source of biogas to said pre-processing system, and within said pre-processing system, processing said source of biogas to produce said pre-processed biogas; and supplying said pre-processed biogas to said biogas acid removal system as said acid-laden biogas, to produce said acid-depleted biogas.

In embodiments, said pre-processing system comprises one or more processing systems selected from the group consisting of a water removal process, pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a pressure-swing adsorption process, a temperature swing adsorption water removal process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

In embodiments, the method further comprises:

providing a post-processing system configured to accept said acid-depleted biogas from said biogas acid removal system and process said acid-depleted biogas in said post-processing system to produce a product; and supplying said acid-depleted biogas from said biogas acid removal system to said post-processing system, and within said post-processing system, processing said acid-depleted biogas to produce said product.

In embodiments, said post-processing system comprises one or more processing systems selected from the group consisting of a water removal process, pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a pressure-swing adsorption process, a temperature swing adsorption water removal process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

In embodiments, the method further comprises:

providing a post-processing system configured to accept said acid-depleted biogas from said biogas acid removal system and process said acid-depleted biogas in said post-processing system to produce a product; and supplying said acid-depleted biogas from said biogas acid removal system to said post-processing system, and within said post-processing system, processing said acid-depleted biogas to produce said product.

In embodiments, said post-processing system comprises one or more processing systems selected from the group consisting of water removal process, pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a pressure-swing adsorption process, a temperature swing adsorption water removal process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

In embodiments, said pre-processing system comprises one or more processing systems selected from the group consisting of a water removal process, pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a pressure-swing adsorption process, a temperature swing adsorption water removal process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

In embodiments, said product comprises one or more products selected from the group consisting of renewable natural gas, a chemical, dimethyl ether, ethanol, Fischer-Tropsch product, hydrogen, methanol, mixed alcohols, an alcohol, 1-butanol, 2-butanol, jet fuel, gasoline, a liquid fuel, diesel, and power.

In embodiments, the method further comprises:

providing a pre-processing system configured to accept a source of biogas, said source of biogas further comprises oxygen, and halogenated volatile organic compounds, and to subject said source of biogas to a combustion process within said pre-processing system to produce a pre-processed biogas; said pre-processed biogas comprises a reduced amount of said oxygen, and a reduced amount of said halogenated volatile organic compounds relative to said source of biogas, wherein a halogen portion of said halogenated volatile organic compounds is disassociated into said halogen by said combustion process, wherein said halogen combines with water vapor within said pre-processed biogas to produce an acid, said pre-processed biogas comprises said acid, and said pre-processing system is further configured to evacuate said pre-processed biogas from said pre-processing system and to supply said pre-processed biogas said biogas acid removal system;

supplying a source of biogas to said pre-processing system, and within said pre-processing system, subjecting said source of biogas to said combustion process to produce said pre-processed biogas, said pre-processed biogas comprises a reduced amount of said oxygen, and a reduced amount of said halogenated volatile organic compounds relative to said source of biogas, wherein said halogen portion of said halogenated volatile organic compound is disassociated into said halogen by said combustion process, wherein said halogen combines with said water vapor within said pre-processed biogas to produce said acid; and supplying said pre-processed biogas to said biogas acid removal system as said acid-laden biogas, to produce said acid-depleted biogas.

In embodiments, said acid-depleted biogas further comprises water vapor; and said method further comprises:

providing a post-processing system configured to accept said acid-depleted biogas and to remove water vapor from said acid-depleted biogas to produce a product; and supplying said acid-depleted biogas from said biogas acid removal system to said post-processing system, and within said post-processing system, removing said water vapor from said acid-depleted biogas to produce said product.

In embodiments, the method further comprises condensing said water vapor removed from said acid-depleted biogas within said post-processing into liquid water comprising an acid; and neutralizing said acid within said liquid water with a base.

In embodiments, said acid-laden biogas is one or more selected from the group consisting of:

acid-laden biogas produced in and collected from an anerobic digester;

acid-laden biogas produced in and collected from a landfill; and acid-laden biogas produced in and collected from a waste water treatment facility.

In embodiments, said acid removal material comprises an adsorbent.

In embodiments, said acid removal material comprises one or more materials selected from the group consisting of activated alumina, activated carbon, alumina, caustic, carbon, carbon nanotubes, catalyst, ceramic material, chitosan, chitin, clay, a dry scrubbing agent, an engineered reactant, iron sponge, an ion-exchange resin, media, molecular sieve, a polymeric adsorbent, promoted alumina, a reactant, a scavenger, silica gel, a base, a neutralizing agent, a pH buffer, and a zeolite.

In embodiments, said acid removal material comprises spheres comprising a diameter ranging from 0.015625 to 5 inches.

In embodiments, said acid-laden biogas comprises an acid content ranging from 0.0005 to 100,000 parts per million.

In embodiments, said acid-depleted biogas comprises an acid content less than 100,000 parts per billion.

In embodiments, a product production system (1000) for producing a product from a source of biogas (A0), said biogas comprises an acid, the system comprises:

a pre-processing system (A) configured to accept said source of biogas (A0) and to process said biogas (A0) within said pre-processing system (A) to produce a pre-processed biogas (A3), and said pre-processing system (A) being further configured to evacuate said pre-processed biogas (A3) from said pre-processing system (A) and to supply said pre-processed biogas (A3) to a biogas acid removal system (100);

said biogas acid removal system (100) configured to accept said pre-processed gas (A3) from said pre-processing system (A), said biogas acid removal system (100) is configured to remove said acid from said pre-processed biogas (A3) to produce an acid-depleted biogas (55), said biogas acid removal system (100) being further configured to evacuate said acid-depleted biogas (55) from said biogas acid removal system (100) and to supply said acid-depleted biogas (55) to a post-processing system (B), wherein said acid-depleted biogas (55) comprises a reduced amount of said acid relative to said pre-processed biogas (A3); and said post-processing system (B) configured to accept said acid-depleted biogas (55) from said biogas acid removal system (100) and to process said acid-depleted biogas (55) within said post-processing system (B) to produce said product (B3).

In embodiments, said biogas acid removal system (100) comprises an acid removal material (40), and within said biogas acid removal system (100) contacting said pre-processed biogas (A3) with said acid removal material (40) to remove at least a portion of said acid from said pre-processed biogas (A3) to produce said acid-depleted biogas (55); wherein:

said acid removal material (40) comprises one or more materials selected from the group consisting of activated alumina, activated carbon, alumina, caustic, carbon, carbon nanotubes, catalyst, ceramic material, chitosan, chitin, clay, a dry scrubbing agent, an engineered reactant, iron sponge, an ion-exchange resin, media, molecular sieve, a polymeric adsorbent, promoted alumina, a reactant, a scavenger, silica gel, a base, a neutralizing agent, a pH buffer, and a zeolite In embodiments, said pre-processing system (A) is configured to process said source of biogas (A0) to produce said pre-processed biogas (A3) by one or more processing systems selected from the group consisting of a water removal process, pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a pressure-swing adsorption process, a temperature swing adsorption water removal process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

In embodiments, said post-processing system (B) is configured to process said acid-depleted biogas (55) to produce said product (B3) by one or more processing systems selected from the group consisting of a water removal process, pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a pressure-swing adsorption process, a temperature swing adsorption water removal process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

In embodiments, said pre-processing system (A) is configured to process said source of biogas (A0) to produce said pre-processed biogas (A3) by one or more processing systems selected from the group consisting of a water removal process, pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a pressure-swing adsorption process, a temperature swing adsorption water removal process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms; and said post-processing system (B) is configured to process said acid-depleted biogas (55) to produce said product (B3) by one or more processing systems selected from the group consisting of a water removal process, pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a pressure-swing adsorption process, a temperature swing adsorption water removal process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

BRIEF DESCRIPTION OF THE DRAWINGS

The accompanying figures show schematic process flow-charts of preferred embodiments and variations thereof. A full and enabling disclosure of the content of the accompanying claims, including the best mode thereof to one of ordinary skill in the art, is set forth more particularly in the remainder of the specification, including reference to the accompanying figures showing how the preferred embodiments and other non-limiting variations of other embodiments described herein may be carried out in practice, in which:

DETAILED DESCRIPTION

Reference will now be made in detail to various embodiments of the disclosure. Each embodiment is provided by way of explanation of the disclosure, not limitation of the disclosure. In fact, it will be apparent to those skilled in the art that modifications and variations can be made in the disclosure without departing from the teaching and scope thereof. For instance, features illustrated or described as part of one embodiment to yield a still further embodiment derived from the teaching of the disclosure. Thus, it is intended that the disclosure or content of the claims cover such derivative modifications and variations to come within the scope of the disclosure or claimed embodiments described herein and their equivalents.

Additional objects and advantages of the disclosure will be set forth in part in the description which follows, and in part will be obvious from the description, or may be learned by practice of the claims. The objects and advantages of the disclosure will be attained by means of the instrumentalities and combinations and variations particularly pointed out in the appended claims.

FIG. 1

Figure 1:
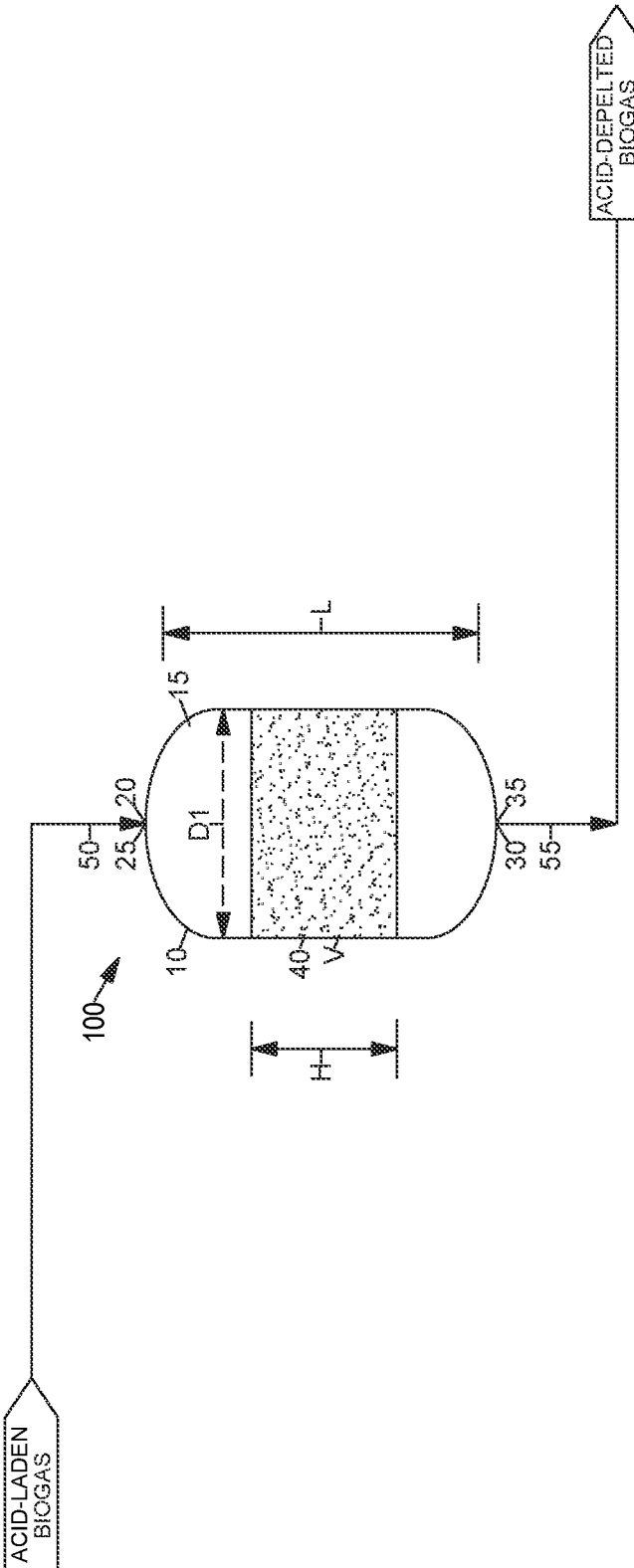
FIG. 1 depicts a non-limiting embodiment of a biogas acid removal system (100) for use in removing acid from biogas.

FIG. 1 depicts a non-limiting embodiment of a biogas acid removal system (100) for use in removing acid from biogas.

In embodiments, the biogas acid removal system (100) comprises an acid removal material (40) for removing acid from the biogas by contacting said biogas with said acid removal material (40) within said biogas acid removal system (100).

In embodiments, the biogas acid removal system (100) comprises a vessel (10) comprising an acid removal material (40). In embodiments, the vessel (10) comprises an adsorber including an acid removal material (40) comprising an adsorbent. In embodiments, the vessel (10) includes an interior (15) with an acid removal material (40) contained within the interior (15).

In embodiments, the vessel (10) is vertically-oriented and comprises a top (25) and a bottom (35). In embodiments, the vessel (10) has an inlet (20) at the top (25) and an outlet (30) at the bottom (35). In embodiments, the vessel (10) has an inlet (20) at the bottom (35) and an outlet (30) at the top (25). In embodiments, an acid-laden biogas (50) is supplied to the inlet (20) of the vessel (10) and an acid-depleted biogas (55) is evacuated from the interior (15) of the vessel (10) via the outlet (30). In embodiments, the vessel (10) comprises a system that is not vertically-oriented wherein the top (25) is a first end and the bottom (35) is a second end where an acid-depleted biogas exits.

In embodiments, the vessel (10) accepts an acid-laden biogas (50) which travels down through the vessel (10) from the top (25) to the bottom (35). In embodiments, the vessel (10) accepts an acid-laden biogas (50) which travels upwards through the vessel (10) from the bottom (35) to the top (25).

In embodiments, the acid-laden biogas (50) includes a biogas, comprising methane and an acid, and the biogas is provided to the biogas acid removal system (100) wherein the biogas contacts the acid removal material (40) within the biogas acid removal system (100) to remove the acid from the biogas to produce an acid-depleted biogas (55), wherein the acid-depleted biogas (55) comprises a reduced amount of the acid relative to the acid-laden biogas (50).

In embodiments, the acid includes an organic acid. In embodiments, non-limiting examples of the organic acid comprise one or more organic acids selected from the group consisting of abietic acid, acetic acid, adipic acid, azelaic acid, barbituric acid, benzoic acid, butyric acid, cacodylic acid, camphoric acid, cinnamic acid, citric acid, cyanuric acid, decanoic acid, diglycolic acid, formic acid, gallic acid, gluconic acid, glycerophosphoric acid, glycolic acid, humic acid, isobutyric acid, lactic acid, maleic acid, malic acid, mandelic acid, oxalic acid, pamoic acid, phthalic acid, picric acid, p-toluenesulfonic acid, salicylic acid, succinic acid, tannic acid, tartaric acid, tartronic acid, tetronic acid, thiodiglycolic acid, thiosalicylic acid, tiglic acid, trichloroacetic acid, trifluoroacetic acid, valeric acid, and vanillic acid.

In embodiments, the acid includes an inorganic acid. In embodiments, non-limiting examples of the inorganic acid comprise one or more inorganic acids selected from the group consisting of boric acid, chlorosulfonic acid, chromosulfuric acid, fluoroboric acid, fluosilicic acid, hydriodic acid, hydrobromic acid, hydrochloric acid, hydrofluoric acid, iodic acid, metaphosphoric acid, nitric acid, perchloric acid, periodic acid, phosphomolybdic acid, phosphoric acid, phosphorous acid, phosphotungstic acid, polyphosphoric acid, selenous acid, silicic acid, sulfamic acid, sulfuric acid, and sulfurous acid. In embodiments, the acid includes a sulfonic acid.

In embodiments, an acid-laden biogas (50) is supplied to the inlet (20) at the top (25) of the vessel (10) and an acid-depleted biogas (55) is transferred from the interior (15) of the vessel (10) via the outlet (30) at the bottom (35).

Acid is removed from the acid-laden biogas (50), which includes a biogas, and/or a portion of a biogas, by utilizing the acid removal material (40) to remove acid from the biogas to produce an acid-depleted biogas (55) which is then evacuated from the vessel (10). The acid-depleted biogas (55) has a lesser amount of the acid relative to the acid-laden biogas (50). Ideally complete removal of acid is desired however some residual amount of the acid may slip-through and not become completely removed by the acid removal material (40) within the biogas acid removal system (100), and therefore part per billion level or a part per million amount of the acid may be present in the biogas that is evacuated from the biogas acid removal system (100). In embodiments, the acid-depleted biogas (55) has a reduced amount of acid relative to the acid-laden biogas (50). A gas quality sensor may be provided to monitor the concentration of acid in the biogas (55) discharged from the biogas acid removal system (100).

In embodiments, the vessel (10) comprises a diameter (D1) and a vessel length (L). The acid removal material (40) within the interior (15) of the vessel (10) comprises a material volume (V) and comprises a material height (H) within the vessel (10). In embodiments, the diameter (D1) of the vessel (10) comprises one or more selected from the group consisting of 0.125 to 0.25 foot, 0.25 to 1 foot, 1 to 2 feet, 2 to 3 feet, 3 to 4 feet, 4 to 5 feet, 5 to 6 feet, 6 to 7 feet, 7 to 8 feet, 8 to 9 feet, 9 to 10 feet, 10 to 12 feet, 12 to 14 feet, 14 to 16 feet, 16 to 18 feet, and 18 to 20 feet.

In embodiments, the material height (H) within the interior (15) of the vessel (10) comprises one or more selected from the group consisting of 6 inches to 1 foot, 1 to 2 feet, 2 to 3 feet, 3 to 4 feet, 4 to 5 feet, 5 to 6 feet, 6 to 7 feet, 7 to 8 feet, 8 to 9 feet, 9 to 10 feet, 10 to 11 feet, 11 to 12 feet, 12 to 13 feet, 13 to 14 feet, 14 to 15 feet, 15 to 16 feet, 16 to 17 feet, 17 to 18 feet, 18 to 19 feet, 19 to 20 feet, 20 to 25 feet, 25 to 30 feet, 30 to 35 feet, 35 to 40 feet, 40 to 45 feet, and 45 to 50 feet. In embodiments, the diameter (D1) is 5 feet, the material height (H) is 15 feet, and the material volume (V) comprises 295 cubic feet of the acid removal material (40). In embodiments, the diameter (D1) of the vessel (10) ranges from 3 to 8 feet, the material height (H) ranges from 10 to 25 feet, and the material volume (V) ranges from 71 to 1256 cubic feet of the acid removal material (40).

In embodiments, the material volume (V) within the interior (15) of the vessel (10) comprises one or more selected from the group consisting of 0.05 to 0.5 cubic feet, 0.5 to 4 cubic feet, 4 to 12 cubic feet, 12 to 16 cubic feet, 16 to 24 cubic feet, 24 to 35 cubic feet, 35 to 47 cubic feet, 47 to 63 cubic feet, 63 to 94 cubic feet, 94 to 98 cubic feet, 98 to 106 cubic feet, 106 to 141 cubic feet, 141 to 188 cubic feet, 188 to 192 cubic feet, 192 to 212 cubic feet, 212 to 251 cubic feet, 251 to 295 cubic feet, 295 to 318 cubic feet, 318 to 377 cubic feet, 377 to 393 cubic feet, 393 to 424 cubic feet, 424 to 565 cubic feet, 565 to 577 cubic feet, 577 to 589 cubic feet, 589 to 754 cubic feet, 754 to 770 cubic feet, 770 to 848 cubic feet, 848 to 954 cubic feet, 954 to 1005 cubic feet, 1005 to 1155 cubic feet, 1155 to 1178 cubic feet, 1178 to 1272 cubic feet, 1272 to 1508 cubic feet, 1508 to 1571 cubic feet, 1571 to 1696 cubic feet, 1696 to 1909 cubic feet, 1909 to 2309 cubic feet, 2309 to 2356 cubic feet, 2356 to 3016 cubic feet, 3016 to 3393 cubic feet, 3393 to 3817 cubic feet, 3817 to 4618 cubic feet, 4618 to 4712 cubic feet, 4712 to 6032 cubic feet, 6032 to 7634 cubic feet, and 7634 to 9425 cubic feet.

In embodiments, the acid removal material (40) comprises one or more materials selected from the group consisting of an adsorbent, activated alumina, activated carbon, alumina, caustic, carbon, carbon nanotubes, catalyst, ceramic material, chitosan, chitin, clay, a dry scrubbing agent, an engineered reactant, iron sponge, an ion-exchange resin, media, molecular sieve, a polymeric adsorbent, promoted alumina, a reactant, a scavenger, silica gel, a base, a neutralizing agent, a pH buffer, and a zeolite. In embodiments, the acid removal material (40) comprises an adsorbent. In embodiments, the acid removal material (40) comprises a molecular sieve. In embodiments, the acid removal material (40) comprises a zeolite. In embodiments, the acid removal material (40) comprises alumina. In embodiments, the biogas acid removal system (100) comprises a scrubber including a caustic material. In embodiments, the biogas acid removal system (100) does not comprise a scrubber including a liquid caustic material.

In embodiments, the biogas acid removal system does not comprise a liquid caustic scrubber. Liquid caustic scrubbers are often too expensive, and include cost-prohibitive long term capital and operating costs. Often times, liquid caustic scrubbers are susceptible to operational problems not only including inadequate liquid flow (maldistribution, channeling, and flooding), entrainment of the liquid caustic scrubbing solution to downstream unit operations (leading to corrosion, contamination, and unexpected plant down-time for maintenance), poor biogas to liquid contact, and plugging of the scrubber internals. Further liquid caustic scrubbers can exhibit scale deposition from minerals used in the scrubbing solution, and necessitate the need for expensive and cumbersome waste water treatment requirements of spend caustic scrubbing solution such as neutralization of the liquid waste for disposal.

In embodiments, said acid removal material (40) comprises a substance configured to neutralize or remove acid from a source of biogas. In embodiments, said acid removal material (40) comprises a base. In embodiments, said acid removal material (40) comprises one or more bases selected from the group consisting of a hydroxide, calcium hydroxide, sodium hydroxide, calcium oxide, sodium bicarbonate, ammonia, sodium carbonate, and potassium hydroxide.

In embodiments, said acid removal material (40) comprises a substance having a pH greater than or equal to 7. In embodiments, said acid removal material (40) comprises a substance having a pH comprising a range selected from the group consisting of 7 to 7.25, 7.25 to 7.5, 7.5 to 7.75, 7.75 to 8, 8 to 8.25, 8.25 to 8.5, 8.5 to 8.75, 8.75 to 9, 9 to 9.25, 9.25 to 9.5, 9.5 to 9.75, 9.75 to 10, 10 to 10.25, 10.25 to 10.5, 10.5 to 10.75, 10.75 to 11, 11 to 11.25, 11.25 to 11.5, 11.5 to 11.75, 11.75 to 12, 12 to 12.25, 12.25 to 12.5, 12.5 to 12.75, 12.75 to 13, 13 to 13.25, 13.25 to 13.5, 13.5 to 13.75, and 13.75 to 14. In embodiments, said acid removal material (40) comprises a substance having a pH greater than 14.

In embodiments, said acid removal material (40) comprises a mixture of water and one or more bases selected from the group consisting of: calcium hydroxide, sodium hydroxide, calcium oxide, sodium bicarbonate, ammonia, sodium carbonate, and potassium hydroxide. In embodiments, said acid removal material (40) comprises a mixture of a solvent and one or more bases selected from the group consisting of: calcium hydroxide, sodium hydroxide, calcium oxide, sodium bicarbonate, ammonia, sodium carbonate, and potassium hydroxide.

In embodiments, said acid removal material (40) comprises a solvent. In embodiments, said acid removal material (40) comprises mixture of a solvent and water. In embodiments, said acid removal material (40) comprises a neutralizing agent. In embodiments, said neutralizing agent neutralizes the acid within the source of biogas with a neutral solution. In embodiments, said neutralizing agent comprises an inorganic compound, wherein said inorganic compound reacts with the acid to neutralize the acid. In embodiments, non-limiting examples of said neutralizing agent include one or more selected from the group consisting of a hydroxide, calcium carbonate, sodium bicarbonate, magnesium oxide, calcium oxide, sodium hydroxide, potassium hydroxide, ammonium hydroxide, sodium carbonate, and potassium carbonate.

In embodiments, said acid removal material (40) comprises a pH buffer. In embodiments, said pH buffer includes a zwitterionic buffer. In embodiments, said pH buffer includes a non-zwitterionic buffer. In embodiments, said pH buffer includes a buffer suitable for cell culture. In embodiments, the vessel (10) within the biogas acid removal system (100) comprises a bioreactor including microorganisms. In embodiments, the microorganisms within the bioreactor produce a substance. In embodiments, the bioreactor removes an acid from the biogas to produce an acid-depleted biogas (55).

In embodiments, the acid removal material (40) comprises individual elements comprising cylinders, powder, particulate, granular particles, rings, packing, tablets, and/or pellets. In embodiments, each individual element of the acid removal material (40) comprises alumina spheres comprising a diameter. In embodiments, the acid removal material (40) comprises spheres comprising a diameter. In embodiments, the acid removal material (40) comprises elements comprising a diameter of $\frac{1}{17}$ to $\frac{1}{8}$ inches. In embodiments, the acid removal material (40) comprises elements comprising a diameter of $\frac{2}{25}$ to $\frac{3}{16}$ inches. In embodiments, the acid removal material (40) comprises elements comprising a diameter of comprising one or more selected from the group consisting of 0.01 to 0.1 inch, 0.1 to 0.25 inch, 0.25 to 0.5 inch, 0.5 to 0.75 inch, 0.75 to 1 inch, 1 to 2 inches, 2 to 3 inches, 3 to 4 inches, and 4 to 5 inches.

In embodiments, the acid removal material (40) comprises a surface area in square meters per gram ranging from one or more selected from the group consisting of 40 to 60, 60 to 80, 80 to 100, 100 to 120, 120 to 140, 140 to 160, 160 to 180, 180 to 200, 200 to 220, 220 to 240, 240 to 260, 260 to 280, 280 to 300, 300 to 400, 400 to 500, 500 to 600, 600 to 700, 700 to 800, 800 to 900, 900 to 1000, 1000 to 1100, 1100 to 1200, 1200 to 1300, 1300 to 1400, 1400 to 1500, 1500 to 1600, 1600 to 1700, 1700 to 1800, 1800 to 1900, 1900 to 2000, 2000 to 2100, 2100 to 2200, 2200 to 2300, 2300 to 2400, 2400 to 2500, 2500 to 2600, 2600 to 2700, 2700 to 2800, 2800 to 2900, 2900 to 3000, 3000 to 3100, 3100 to 3200, 3200 to 3300, 3300 to 3400, 3400 to 3500, 3500 to 3600, 3600 to 3700, 3700 to 3800, 3800 to 3900, 3900 to 4000, 4000 to 4100, 4100 to 4200, 4200 to 4300, 4300 to 4400, 4400 to 4500, 4500 to 4600, 4600 to 4700, 4700 to 4800, 4800 to 4900, and 4900 to 5000 square meters per gram.

In embodiments, the acid removal material (40) comprises a crush strength ranging from one or more selected from the group consisting of 0.1 to 1 pound force (lbf), 1 to 10 lbf, 10 to 11 lbf, 11 to 12 lbf, 12 to 13 lbf, 13 to 14 lbf, 14 to 15 lbf, 15 to 16 lbf, 16 to 17 lbf, 17 to 18 lbf, 18 to 19 lbf, 19 to 20 lbf, 20 to 21 lbf, 21 to 22 lbf, 22 to 23 lbf, 23 to 25 lbf, 25 to 30 lbf, 30 to 40 lbf, 40 to 50 lbf, 50 to 60 lbf, 60 to 70 lbf, 70 to 80 lbf, 80 to 90 lbf, 90 to 100 lbf, 100 to 500 lbf, 500 to 1000 lbf, 1000 to 5000 lbf, 5000 to 10000 lbf, 10000 to 15000 lbf, 15000 to 20000 lbf, and 20000 to 25000 lbf.

In embodiments, the acid removal material (40) comprises alumina, and comprises one or more alumina weight percent selected from the group consisting of 0 to 5 weight percent, 5 to 15 weight percent, 15 to 30 weight percent, 30 to 60 weight percent, 60 to 80 weight percent, 80 to 82 weight percent, 82 to 84 weight percent, 84 to 86 weight percent, 86 to 88 weight percent, 88 to 90 weight percent, 90 to 92 weight percent, 92 to 94 weight percent, 94 to 96 weight percent, 96 to 98 weight percent, 98 to 99.95 weight percent, and 99.95 to 100 weight percent. In embodiments, the acid removal material (40) comprises alumina, wherein said acid removal material (40) comprises an adsorbent that comprises 88 to 96 weight percent alumina.

In embodiments, the acid removal material (40) comprises alumina, wherein said adsorbent comprises one or more alumina weight percent selected from the group consisting of 0 to 5 weight percent, 5 to 10 weight percent, 10 to 15 weight percent, 15 to 20 weight percent, 20 to 25 weight percent, 25 to 30 weight percent, 30 to 35 weight percent, 35 to 40 weight percent, 40 to 45 weight percent, 45 to 50 weight percent, 50 to 55 weight percent, 55 to 60 weight percent, 60 to 65 weight percent, 65 to 70 weight percent, 70 to 75 weight percent, 75 to 80 weight percent, 80 to 85 weight percent, 85 to 90 weight percent, 90 to 95 weight percent, and 95 to 100 weight percent.

In embodiments, the acid removal material (40) comprises a promoted alumina comprising a promoter, wherein said acid removal material (40) comprises one or more promoter weight percent selected from the group consisting of 0 to 2 weight percent, 2 to 4 weight percent, 4 to 6 weight percent, 6 to 8 weight percent, 8 to 10 weight percent, 10 to 12 weight percent, 12 to 14 weight percent, 14 to 16 weight percent, 16 to 18 weight percent, 18 to 20 weight percent, 20 to 25 weight percent, 25 to 30 weight percent, 30 to 35 weight percent, 35 to 40 weight percent, 40 to 45 weight percent, 45 to 50 weight percent, 50 to 55 weight percent, 55 to 60 weight percent, 60 to 65 weight percent, 65 to 70 weight percent, 70 to 75 weight percent, 75 to 80 weight percent, 80 to 85 weight percent, 85 to 90 weight percent, 90 to 95 weight percent, and 95 to 100 weight percent.

In embodiments, the promoter within the acid removal material (40) is a substance that increases the rate at which another substance adheres, interacts, binds, adsorbs, and/or reacts to it. In embodiments, the acid removal material (40) comprises an adsorbent, and the promoter within the adsorbent is a substance that increases the rate at which another substance adheres, interacts, binds, adsorbs, and/or reacts to it. In embodiments, the promoter can be used to increase the efficiency of removal, or adsorption, of said acid by increasing the surface area of the material that is in contact with the acid.

In embodiments, there are a variety of different promoters that can be used in the acid removal material (40), not only including metal promoters which include metal ions or metal compounds that are added to the acid removal material (40) to increase its activity, surface area, and/or efficiency. For example, some non-limiting types of metal promoters used in the material include one or more promoters selected from the group consisting of chromium, cobalt, copper, iron, molybdenum, nickel, palladium, platinum, tungsten, and vanadium. These metals can be used alone or in combination with each other or with other types of promoters, such as non-metal or organic promoters.

In embodiments, the flow of the acid-laden biogas (50) and/or acid-depleted biogas (55) entering and/or leaving the vessel (10) includes one or more flowrates selected from the group consisting of 1 to 25 standard cubic feet per minute (SCFM), 25 to 100 SCFM, 100 to 500 SCFM, 500 to 1000 SCFM, 1000 to 2000 SCFM, 2000 to 3000 SCFM, 3000 to 4000 SCFM, 4000 to 5000 SCFM, 5000 to 6000 SCFM, 6000 to 7000 SCFM, 7000 to 8000 SCFM, 8000 to 9000 SCFM, 9000 to 10000 SCFM, 10000 to 15000 SCFM, and 15000 to 20000 SCFM.

In embodiments, the acid removal material (40) is a non-regenerable material and is changed-out over a time duration, said time duration comprises one or more time durations selected from the group consisting of: 1 to 2 months, 2 to 3 months, 3 to 4 months, 4 to 5 months, 5 to 6 months, 6 to 8 months, 8 months to 1 year, 1 to 1.5 years, 1.5 to 2 years, 2 to 2.5 years, 2.5 to 3 years, 3 to 3.5 years, 3.5 to 4 years, 4 to 4.5 years, 4.5 to 5 years, 5 to 6 years, 6 to 7 years, 7 to 8 years, 8 to 9 years, 9 to 10 years, and 10 to 15 years.

In embodiments, the acid removal material (40) is a non-regenerable material and instead is used in a single-use application and is not intended nor designed to be regenerated. In embodiments, the acid removal material (40) comprises a regenerable material. In embodiments, the acid removal material (40) comprises an adsorbent and includes a regenerable sorbent which may be regenerated by removing the acid that has been adsorbed onto the surface or into pores of the adsorbent. This can be done through a variety of methods, including pressure swing desorption, temperature swing desorption, heating, washing, pulling a vacuum, and/or exposure to a chemical and/or a mixture of chemicals. In embodiments, the acid removal material (40) includes a regenerable adsorbent comprising alumina that can be regenerated by thermal regeneration, chemical regeneration, and/or physical regeneration.

In embodiments, the acid removal material (40) removes the acid from the acid-laden biogas (50) to produce the acid-depleted biogas (55), wherein the acid-depleted biogas (55) comprises an acid content ranging from one or more ranges selected from the group consisting of 0 to 0.0001 parts per million (ppm), 0.0001 to 0.001 ppm, 0.001 to 0.005 ppm, 0.005 to 0.025 ppm, 0.025 to 0.125 ppm, 0.125 to 0.25 ppm, 0.25 to 0.5 ppm, 0.5 to 0.75 ppm, 0.75 to 1 ppm, 1 to 1.25 ppm, 1.25 to 1.5 ppm, 1.5 to 1.75 ppm, 1.75 to 2 ppm, 2 to 2.25 ppm, 2.25 to 2.5 ppm, 2.5 to 2.75 ppm, 2.75 to 3 ppm, 3 to 3.25 ppm, 3.25 to 3.5 ppm, 3.5 to 3.75 ppm, 3.75 to 4 ppm, 4 to 4.25 ppm, 4.25 to 4.5 ppm, 4.5 to 4.75 ppm, 4.75 to 5 ppm, 5 to 5.5 ppm, 5.5 to 6 ppm, 6 to 6.5 ppm, 6.5 to 7 ppm, 7 to 7.5 ppm, 7.5 to 8 ppm, 8 to 8.5 ppm, 8.5 to 9 ppm, 9 to 9.5 ppm, 9.5 to 10 ppm, 10 to 15 ppm, 15 to 20 ppm, 20 to 25 ppm, 25 to 30 ppm, 30 to 35 ppm, 35 to 40 ppm, 40 to 45 ppm, 45 to 50 ppm, 50 to 75 ppm, 75 to 100 ppm, 100 to 125 ppm, 125 to 150 ppm, 150 to 175 ppm, 175 to 200 ppm, 200 to 250 ppm, 250 to 300 ppm, 300 to 350 ppm, 350 to 400 ppm, 400 to 450 ppm, and 450 to 500 ppm.

In embodiments, the acid removal material (40) removes said acid from the acid-laden biogas (50) to produce the acid-depleted biogas (55), wherein the acid-depleted biogas (55) comprises an acid content of 0 parts per billion (ppb).

In embodiments, the acid removal material (40) removes said acid from the acid-laden biogas (50) to produce the acid-depleted biogas (55), wherein the acid-depleted biogas (55) comprises an acid content ranging from one or more ranges selected from the group consisting of 0 to 5 parts per billion (ppb), 5 to 10 ppb, 10 to 15 ppb, 15 to 20 ppb, 20 to 25 ppb, 25 to 30 ppb, 30 to 35 ppb, 35 to 40 ppb, 40 to 45 ppb, 45 to 50 ppb, 50 to 60 ppb, 60 to 70 ppb, 70 to 80 ppb, 80 to 90 ppb, 90 to 100 ppb, 100 to 200 ppb, 200 to 300 ppb, 300 to 400 ppb, 400 to 500 ppb, 500 to 600 ppb, 600 to 700 ppb, 700 to 800 ppb, 800 to 900 ppb, 900 to 1000 ppb, 1000 to 2000 ppb, 2000 to 3000 ppb, 3000 to 4000 ppb, 4000 to 5000 ppb, 5000 to 10000 ppb, 10000 to 20000 ppb, 20000 to 40000 ppb, 40000 to 80000 ppb, and 80000 to 100000 ppb.

In embodiments, the acid-laden biogas (50) comprises an acid content ranging from one or more ranges selected from the group consisting of 0.0005 to 0.05 parts per million (ppm), 0.05 to 1 ppm, 1 to 4 ppm, 4 to 5 ppm, 5 to 10 ppm, 10 to 15 ppm, 15 to 20 ppm, 20 to 25 ppm, 25 to 30 ppm, 30 to 35 ppm, 35 to 40 ppm, 40 to 45 ppm, 45 to 50 ppm, 50 to 60 ppm, 60 to 70 ppm, 70 to 80 ppm, 80 to 90 ppm, 90 to 100 ppm, 100 to 200 ppm, 200 to 300 ppm, 300 to 400 ppm, 400 to 500 ppm, 500 to 1000 ppm, 1000 to 2500 ppm, 2500 to 5000 ppm, 5000 to 10000 ppm, 10000 to 50000 ppm, and 50000 to 100000 ppm.

In embodiments, FIG. 1 describes a method to produce an acid-depleted biogas, comprising:

providing a source of biogas, said biogas comprises methane and an acid;

providing a biogas acid removal system comprising an adsorbent, said biogas acid removal system is configured to accept said source of biogas and contact said source of biogas with said adsorbent to remove at least a portion of said acid within said source of biogas to produce said acid-depleted biogas, said acid-depleted biogas comprises a reduced amount of said acid relative to said source of biogas; and supplying said source of biogas to said biogas acid removal system, and within said biogas acid removal system contacting said source of biogas with said adsorbent to adsorb said at least a portion of said acid from said source of biogas to produce said acid-depleted biogas, wherein said acid-depleted biogas comprises a reduced amount of said acid relative to said source of biogas.

In embodiments, FIG. 1 describes a method to produce an acid-depleted biogas, comprising:

providing a source of biogas, said biogas comprises an acid;

providing a biogas acid removal system comprising an acid removal material, said biogas acid removal system accepts said source of biogas and contacts said source of biogas with said acid removal material within said biogas acid removal system to remove at least a portion of said acid within said source of biogas to produce said acid-depleted biogas, said acid-depleted biogas comprises a reduced amount of said acid relative to said source of biogas; and supplying said source of biogas to said biogas acid removal system, and within said biogas acid removal system contacting said source of biogas with said acid removal material to remove said at least a portion of said acid from said source of biogas to produce said acid-depleted biogas, wherein said acid-depleted biogas comprises a reduced amount of said acid relative to said source of biogas.

In embodiments, said biogas (50) or said acid-laden biogas (50) is derived from gases produced by the biological breakdown of organic matter. In embodiments, said biogas (50) or said acid-laden biogas (50) for example may be derived from one or more sources of organic matter selected from the group consisting of carbonaceous material, biomass, compost, municipal solid waste, refuse derived fuel, garbage, plant matter, sewage, sewage sludge, waste water treatment facility products, industrial waste, energy crops, vinasse, food waste, human excrement, animal manure, pig manure, chicken manure, cow manure, horse manure, bird manure, cattle manure, insect manure, humans, animals, pigs, chickens, cows, horses, bird, and insects.

In embodiments, said biogas (50) or said acid-laden biogas (50) is produced in and/or collected from an anerobic digester and/or an anerobic digestion process. For example, in an anerobic digester and/or an anerobic digestion process biogas is produced through the process of anaerobic digestion.

In embodiments, said biogas (50) or said acid-laden biogas (50) is produced in and/or collected from a landfill.

In embodiments, said biogas (50) or said acid-laden biogas (50) is produced in and/or collected from waste water treatment facility.

In embodiments, the acid removal process from biogas can be used to produce renewable energy products including products and processes that mitigate climate change by capturing of greenhouse gases such as methane (and carbon dioxide, and nitrogen) to make useful products. In embodiments, the acid removal process from biogas can be used to produce renewable energy products including products and processes that mitigate climate change by employing technologies for the production of fuel of non-fossil origin not only including hydrogen, biofuels, synthetic alcohols, synthetic liquid fuels, synthetic chemicals, renewable natural gas, renewable electricity, renewable power, renewable energy. In embodiments, the acid removal process from biogas can be used to produce renewable chemical products including products and processes that mitigate climate change by use of renewable energy sources, improving process efficiency by removing an acid to prevent corrosion of important capital assets within associated systems. In embodiments, the acid removal process from biogas can be used to produce renewable energy products including products and processes that mitigate climate change by employing advancements in technologies relating to agriculture and livestock or agroalimentary industries by using waste plant matter and or waste manure from livestock operations to produce new and useful products. In embodiments, the acid removal process from biogas can be used to produce renewable energy products including products and processes that mitigate climate change by enabling technologies with a potential contribution to greenhouse gas emissions mitigation such as fuel cell and hydrogen production processes. In embodiments, the acid removal process from biogas can be used to produce renewable energy products including products and processes that mitigate climate change by employing landfill technologies aiming to mitigate methane emissions by processing biogas from the landfill instead of allowing the methane and other gases within the biogas to permeate from the landfill surface.

FIG. 2

Figure 2:
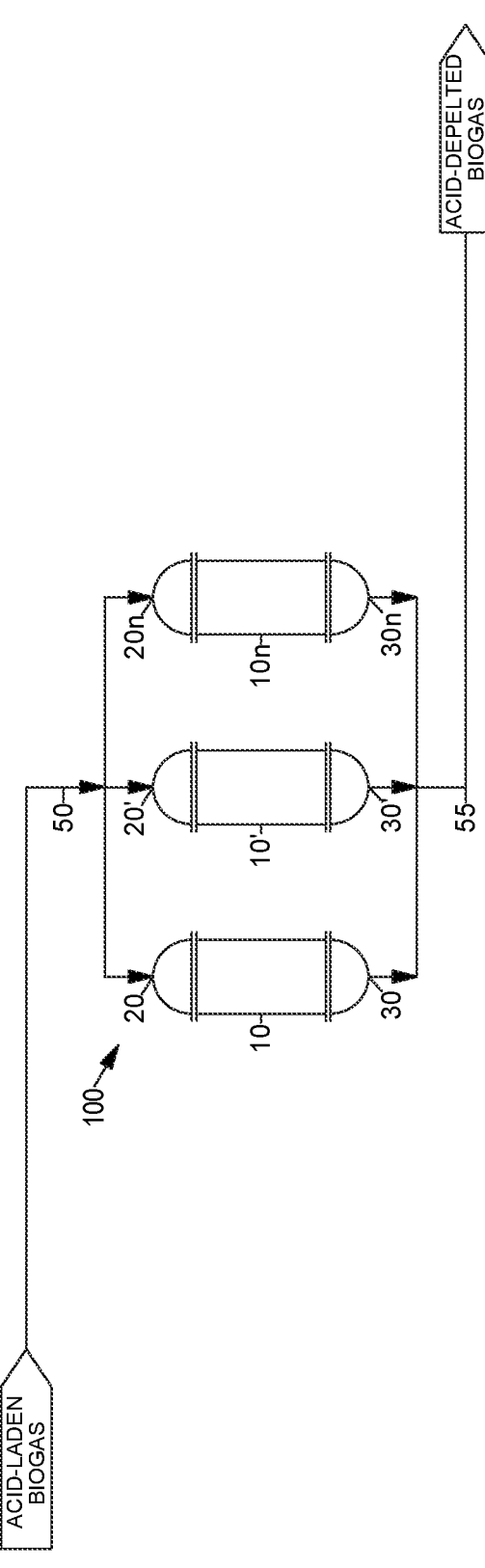
FIG. 2 depicts another non-limiting embodiment of a biogas acid removal system (100) for use in removing acid from biogas.

FIG. 2 depicts another non-limiting embodiment of a biogas acid removal system (100) for use in removing acid from biogas.

FIG. 2 shows a plurality of vessels (10, 10') as depicted in FIG. 1, however shown in parallel. In embodiments, each of the plurality of vessels (10, 10', 10$n$) shown in within the biogas acid removal system (100) of FIG. 2 has an inlet (20, 20', 20$n$) and an outlet (30, 30', 30$n$) and configured to receive the acid-laden biogas (50), remove acid therefrom and produce the acid-depleted biogas (55).

FIG. 2 shows a plurality of vessels (10, 10', 10$n$) connected in parallel where both or one of the plurality of vessels (10, 10') receive at least a portion of the biogas or the acid-laden biogas (50). In embodiments, as shown in FIG. 2. at least one of the plurality of vessels (10, 10', 10$n$) receives a portion of the acid-laden biogas (50) to produce an acid-depleted biogas (55) that comes from a plurality of vessels (10, 10', 10$n$).

In embodiments, as shown in FIG. 2. at least one of the plurality of vessels (10, 10', 10$n$) receives at least a portion of the acid-laden biogas (50), while at least one of the plurality of vessels (10, 10', 10$n$) is in standby-mode awaiting subsequent use at a later time. Although three vessels (10, 10', 10n) are shown in FIG. 2, it is to be understood that two, three, four, five, six, or more vessels (10, 10', 10n) may be provided.

In embodiments, the plurality of vessels (10, 10', 10n) connected in parallel as depicted in FIG. 2 to increase the overall capacity of the system. When the vessels (10, 10', 10n) are connected in parallel, they operate simultaneously and share the load equally. This allows the system to treat a larger volume of biogas in a given period of time, and thus remove more acid from the acid-laden biogas (50).

In embodiments, the plurality of vessels (10, 10', 10n) connected in parallel as depicted in FIG. 2 offers greater flexibility in that parallel vessels can be easily adjusted to meet changing treatment needs, allowing the system to be easily scaled up or down as needed. Reduced maintenance costs also plays a role in utilizing the biogas acid removal system (100) of FIG. 2, for example, the parallel vessels (10, 10', 10n) can extend the life of each individual vessel (10, 10', 10n), as they can operate at a lower flow rate and be regenerated more frequently which can help to reduce the overall cost of the system.

FIG. 3

Figure 3:
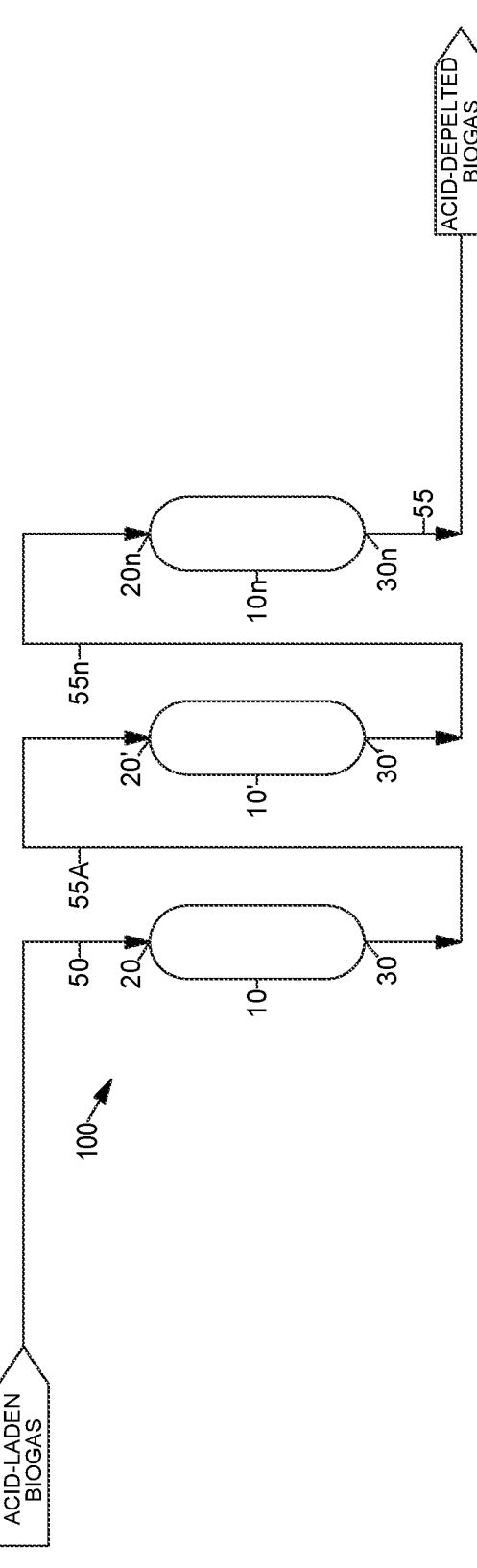
FIG. 3 depicts another non-limiting embodiment of a biogas acid removal system (100) for use in removing acid from biogas.

FIG. 3 depicts another non-limiting embodiment of a biogas acid removal system (100) for use in removing acid from biogas. FIG. 3 shows a plurality of vessels (10, 10', 10n) as depicted in FIG. 1, however shown in series. In embodiments, each of the plurality of vessels (10, 10', 10n) shown in within the biogas acid removal system (100) of FIG. 3 has an inlet (20, 20', 20n) and an outlet (30, 30', 30n). However, FIG. 3 shows the outlet (30) of a first vessel (10) in fluid communication with the inlet (20') of the second vessel (10'), and the outlet (30') of a second vessel (10') in fluid communication with the inlet (20n) of a third vessel (10n). This allows for the acid-laden biogas (50) to first pass through the first vessel (10) to produce a first intermediate acid-depleted biogas (55A), and the first intermediate acid-depleted biogas (55A) is then supplied to the second vessel (10') to further remove (or polish) acid therefrom and produce a second intermediate acid-depleted biogas (55n). The second intermediate acid-depleted biogas (55n) is then supplied to the third vessel (10n) to further remove (or polish) acid therefrom and produce the acid-depleted biogas (55). Although three vessels (10, 10', 10n) are shown in FIG. 3, it is to be understood that two, three, four, five, six, or more vessels (10, 10', 10n) may be provided.

The acid-laden biogas (50) comprises at least methane and an acid. The first intermediate acid-depleted biogas (55A) comprises a reduced amount of acid relative to the acid-laden biogas (50). The second intermediate acid-depleted biogas (55n) comprises a reduced amount of acid relative to both the acid-laden biogas (50) and the first intermediate acid-depleted biogas (55A). The acid-depleted biogas (55) comprises a reduced amount of acid relative to the first and second intermediate acid-depleted biogas (55A, 55n).

The biogas acid removal system (100) as shown in FIG. 3 depicts a lead-lag vessel configuration where the first vessel (10) receives the acid-laden biogas (50) to remove acid therefrom and produce a first intermediate acid-depleted biogas (55A), a second vessel (10') receives the first intermediate acid-depleted biogas (55A) and removes acid therefrom to produce a second intermediate acid-depleted biogas (55n), and a third vessel (10n) receives the second intermediate acid-depleted biogas (55n) and removes acid therefrom to produce an acid-depleted biogas (55). In embodiments, this lead-lag vessel arrangement as shown in FIG. 3 is used to remove acid from a biogas. FIG. 3 shows three vessels (10, 10', 10n) that are connected in series, with the first vessel (10) operating in the "lead" position and the second and third vessels (10', 10n) operating in the "lag" position.

In embodiments, after a duration of time operating where the first vessel (10) receives the acid-laden biogas (50), the second vessel (10') receives the first intermediate acid-depleted biogas (55A), and the third vessel (10n) receives the second intermediate acid-depleted biogas (55n), the first, second, and/or third vessels can be switched, wherein the first vessel (10') which was the "lead" vessel may be switched to the "lag" vessel, and similarly the second vessel (10') and third vessel (10n) which had been operating as the "lag" vessel can be changed to the "lead" vessel. By switching the "lead" vessel to the "lag" vessel, the biogas acid removal system (100) can realize improved efficiency, reduced downtime, greater flexibility, and reduced maintenance costs.

In embodiments: the first vessel (10) is lead, second vessel (10') is first lag, third vessel (10n) is second lag; the second vessel (10') is lead, third vessel (10n) is first lag, first vessel (10) is second lag; the third vessel (10n) is lead, first vessel (10) is first lag, second vessel (10') is second lag.

In embodiments: the first vessel (10) is lead, second vessel (10') is first lag, third vessel (10n) is second lag; the third vessel (10n) is lead, first vessel (10) is first lag, second vessel (10') is second lag; the second vessel (10') is lead, third vessel (10n) is first lag, first vessel (10) is second lag.

In embodiments, there are certain benefits to installing the biogas acid removal system (100) in the configuration of FIG. 3. Use of a plurality of vessels (10, 10', 10n) in series, a lead-lag vessel arrangement can effectively remove a greater amount of acid from the biogas. This can improve the overall efficiency of the treatment process. Lead-lag vessels (10, 10', 10n) as shown in FIG. 3 allow one vessel to continue operating while the other is being regenerated or replaced with fresh acid removal material (40). This can help to reduce downtime and improve the overall reliability of the system. Lead-lag vessels (10, 10', 10n) as shown in FIG. 3 can be easily adjusted to meet changing treatment needs (e.g. variations in acid levels of the biogas entering the biogas acid removal system (100), variations in flow rates or impurity levels). By using a plurality of vessels (10, 10', 10n) in series, a lead-lag vessel can effectively extend the life of acid removal material (40) in each vessel (10, 10', 10n), reducing the need for frequent maintenance and replacement. In embodiments the acid removal material (40) within each of the vessels (10, 10', 10n) is identical. In embodiments, the material (40) within each of the vessels (10, 10', 10n) is different. This can help to reduce the overall cost of the system. In embodiments, the lead-lag configuration as shown in FIG. 3 allows for a downstream second vessel (10') and/or third vessel (10n) to polish the first intermediate acid-depleted biogas (55A) and/or the second intermediate acid-depleted biogas (55n). In embodiments, the second vessel (10') and third vessel (10n) both act as a polishing step, and serve as the final acid removal step in the biogas acid removal system (100). Although three vessels are shown in FIG. 3, only two can be utilized, or more can be arranged in series (e.g. four, five, six, or more).

FIG. 4

Figure 4:
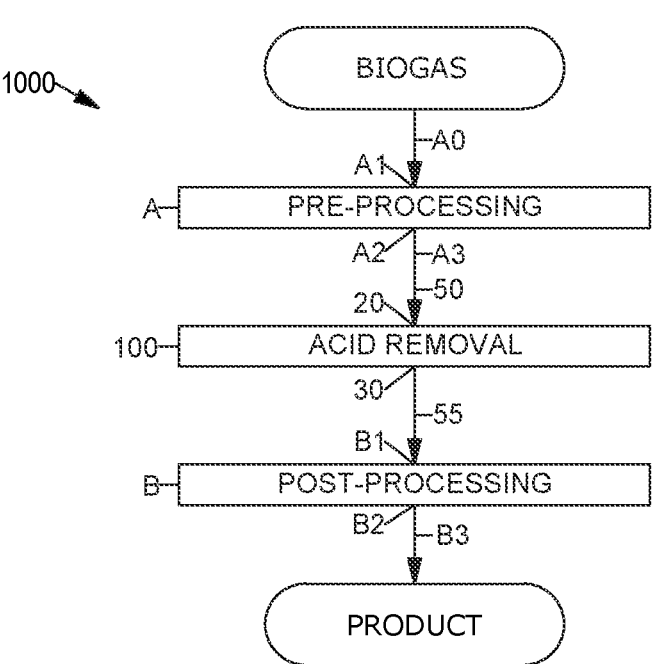
FIG. 4 depicts a non-limiting embodiment of a biogas acid removal system (100) integrated within a product production system (1000) for producing a product from an acid-depleted biogas that has undergone both pre-processing and/or post-processing.

FIG. 4 depicts a non-limiting embodiment of a biogas acid removal system (100) integrated within a product production system (1000) for producing a product from an acid-depleted biogas that has undergone both pre-processing and/or post-processing.

FIG. 4 shows a product production system (1000) configured to produce a product (B3) from a source of biogas (A0). In embodiments, the product production system (1000) of FIG. 4 comprises a pre-processing system (A), a biogas acid removal system (100), and a post-processing system (B). In embodiments, the product production system (1000) of FIG. 4 comprises:

a pre-processing system (A) configured to accept said source of biogas (A0) through inlet (A1) and process said biogas (A0) within said pre-processing system (A) to produce a pre-processed biogas (A3), said pre-processed biogas (A3) is evacuated from said pre-processing system (A) through outlet (A2) and supplied to a biogas acid removal system (100);

said biogas acid removal system (100) at inlet (20) accepts said pre-processed gas (A3) from said pre-processing system (A), said biogas acid removal system (100) removes said acid from said pre-processed biogas (A3) to produce an acid-depleted biogas (55), said acid-depleted biogas (55) is evacuated from outlet (30) of said biogas acid removal system (100) and supplied to a post-processing system (B), wherein said acid-depleted biogas (55) comprises a reduced amount of said acid relative to said pre-processed biogas (A3); and said post-processing system (B) accepts said acid-depleted biogas (55) from said biogas acid removal system (100) through inlet (B1) and processes said acid-depleted biogas (55) within said post-processing system (B) to produce said product (B3), which is evacuated from said post-processing system (B) through outlet (B2).

In embodiments, said product (B3) comprises a one or more products selected from the group consisting of post-processed biogas, renewable natural gas, a chemical, dimethyl ether, ethanol, Fischer-Tropsch product, hydrogen, methanol, mixed alcohols, an alcohol, 1-butanol, 2-butanol, jet fuel, gasoline, diesel, a liquid fuel, and power. In embodiments, the biogas acid removal system (100) comprises a acid removal material (40) wherein said material comprises one or more materials selected from the group consisting of activated alumina, activated carbon, adsorbent, alumina, carbon, carbon nanotubes, catalyst, ceramic material, caustic, chitosan, chitin, clay, a dry scrubbing agent, an engineered reactant, iron sponge, an ion-exchange resin, molecular sieve, polymeric adsorbent, promoted alumina, reactant, a scavenger, silica gel, and a zeolite.

In embodiments, the biogas acid removal system (100) comprises an acid removal material (40) and within said biogas acid removal system (100), contacting said pre-processed biogas (A3) or said acid-laden biogas (50), with said acid removal material (40) to remove acid from said pre-processed biogas (A3), or said acid-laden biogas (50), to remove at least a portion of said acid within said pre-processed biogas (A3), or said acid-laden biogas (50), to produce said acid-depleted biogas (55), wherein said acid-depleted biogas (55) comprises a reduced amount of said acid relative to said pre-processed biogas (A3) or said acid-laden biogas (50).

In embodiments, the pre-processing system (A) processes said biogas (A0) to produce a pre-processed biogas (A3), or an acid-laden biogas (50), by one or more processes systems selected from the group consisting of water removal process, pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a pressure-swing adsorption process, a temperature swing adsorption water removal process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

In embodiments, the post-processing system (B) processes said acid-depleted biogas (55) to produce a product (B3) by one or more processes systems selected from the group consisting of water removal process, pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a pressure-swing adsorption process, a temperature swing adsorption water removal process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

In embodiments, the microorganisms within the bioreactor produce a substance. In embodiments, the microorganisms within the bioreactor produce one or more substances, selected from the group consisting of a chemical, an alcohol, ethanol, 1-butanol, and 2-butanol, within the bioreactor.

In embodiments, the chemical produced in the bioreactor includes one or more selected from the group consisting of: 3-hydroxypropionate; mevalonate; mevalonic acid; isoprene; aromatics; benzoate (p-hydroxyl, 2-amino, dihydroxy); salicylate; 1-propanol; 1,2-propanediol; (R)-1,2-propanediol; (S)-1,2-propanediol; mixed isomers of 1,2-propanediol; acetoin; methyl ethyl ketone; branched-chain amino acids; valine, leucine, isoleucine; succinate; lactate; 2,3-butanediol; (R,R)-2,3-butanediol; meso-2,3-butanediol; mixed isomers of 2,3-butanediol; citramalate; 1,3-butanediol; (R)-1,3-butanediol; (S)-1,3-butanediol; mixed isomers of 1,3-butanediol; 3-hydroxybutyrate; (R)-3-hydroxybutyrate; (S)-3-hydroxybutyrate; mixed isomers of 3-hydroxybutyrate; butyrate; acetone; isopropanol; acetate; 1,3-butadiene; biopolymers; isobutene; and long chain alcohols.

In embodiments, the substance produced in the bioreactor is then distilled. In embodiments, the substance produced in the bioreactor is then removed using a membrane. In embodiments, the substance produced in the bioreactor is then dehydrated using pressure swing adsorption. In embodiments, the substance produced in the bioreactor is then dehydrated using an adsorbent. In embodiments, the substance produced in the bioreactor is then dehydrated using 3 angstrom molecular sieves.

In embodiments, when ethanol is produced in the bioreactor, it is then distilled. In embodiments, the ethanol produced in the bioreactor is then removed using a membrane. In embodiments, the ethanol produced in the bioreactor is then dehydrated using pressure swing adsorption. In embodiments, the ethanol produced in the bioreactor is then dehydrated using an adsorbent. In embodiments, the ethanol produced in the bioreactor is then dehydrated using 3 angstrom molecular sieves.

In embodiments, the bioreactor includes one or more type of bioreactors selected from the group consisting of a continuous stirred tank bioreactor, a bubble column bioreactor, a microbubble reactor, an airlift bioreactor, a fluidized bed bioreactor, a packed bed bioreactor, a photo-bioreactor, and combinations thereof. In embodiments, the microorganisms used within the bioreactor include genetically modified organisms. In embodiments, the microorganisms used within the bioreactor do not include genetically modified organisms. In embodiments, the microorganisms used within the bioreactor include gas fermenting organisms. In embodiments, the microorganisms used within the bioreactor undergo anaerobic respiration. In embodiments, the microorganisms used within the bioreactor undergo fermentation. In embodiments, the microorganisms used within the bioreactor include anaerobic bacteria. In embodiments, the bioreactor includes a liquid nutrient medium used for culturing the microorganisms and the substance is produced within the bioreactor by the microorganisms which secrete the substance which accumulates within the liquid nutrient medium. In embodiments, the substance is upgraded into a liquid fuel such as a chemical, dimethyl ether, ethanol, Fischer-Tropsch product, methanol, mixed alcohols, an alcohol, 1-butanol, 2-butanol, jet fuel, gasoline, a liquid fuel, and/or diesel.

In embodiments, the post-processing system (B) processes said acid-depleted biogas (55) to produce a product (B3), wherein said product (B3) comprises a one or more products selected from the group consisting of post-processed biogas, renewable natural gas, a chemical, a liquid fuel, dimethyl ether, ethanol, Fischer-Tropsch product, hydrogen, methanol, mixed alcohols, and power.

In embodiments, halogenated volatile organic compounds are included within the biogas (A0) supplied to the pre-processing system (A). In embodiments, the halogenated volatile organic compounds are subjected to processing within the pre-processing system (A), wherein said halogen portion within the halogenated volatile organic compound is disassociated from the halogenated volatile organic compound and is converted into an acid. As a result, the disassociated halogen merges with a water molecule to form the acid, and the acid is then removed from the pre-processed biogas in the biogas acid removal system. In embodiments, the halogen is disassociated from the halogenated volatile organic compounds within the pre-processing system that includes a catalytic oxygen reduction process, wherein the source of biogas (A0) is subjected to a combustion step to combust at least a portion of the oxygen with at least a portion of the methane and/or at least a portion of the halogenated volatile organic compounds to produce the pre-processed biogas (A3). In embodiments, the pre-processed biogas (A3) includes combustion products comprising carbon dioxide and water vapor, as well as the acid which merges with the water to for the acid. In embodiments, the pre-processed biogas (A3) includes combustion products comprising carbon dioxide and an acid, wherein the acid is formed during in pre-processing system (A) during the pre-processing of the biogas (A0). In embodiments, the halogen that is included within the halogenated volatile organic compound includes one or more halogens selected from the group consisting of fluorine, chlorine, bromine, iodine, astatine, and ununseptium.

In embodiments, the pre-processing system (A) processes said biogas (A0) to remove oxygen therefrom to produce a pre-processed biogas (A3) or an acid-laden biogas (50). In embodiments, the pre-processing system (A) comprises a catalytic oxygen reduction process to combust any oxygen within said biogas (A0) to produce a pre-processed biogas (A3), or an acid-laden biogas (50), comprising a reduced amount of oxygen relative to said first biogas (A0). In embodiments, combustion of said oxygen within said biogas (A0) produces carbon dioxide and water vapor, wherein said pre-processed biogas (A3) or an acid-laden biogas (50) comprises an acid and a reduced amount of oxygen and an increased amount of carbon dioxide and water vapor relative to said first biogas (A0).

In embodiments, the oxygen concentration in the pre-processed biogas (A3) or an acid-laden biogas (50) includes one or more concentration ranges selected from the group consisting of 0 to 0.1 volume percent of oxygen (vol %), 0.1 to 0.2 vol %, 0.2 to 0.3 vol %, 0.3 to 0.4 vol %, 0.4 to 0.5 vol %, 0.5 to 0.6 vol %, 0.6 to 0.7 vol %, 0.7 to 0.8 vol %, 0.8 to 0.9 vol %, 0.9 to 1 vol %, 1 to 1.1 vol %, 1.1 to 1.2 vol %, 1.2 to 1.3 vol %, 1.3 to 1.4 vol %, 1.4 to 1.5 vol %, 1.5 to 1.6 vol %, 1.6 to 1.7 vol %, 1.7 to 1.8 vol %, 1.8 to 1.9 vol %, 1.9 to 2 vol %, 2 to 2.25 vol %, 2.25 to 2.5 vol %, 2.5 to 2.75 vol %, 2.75 to 3 vol %, 3 to 3.25 vol %, 3.25 to 3.5 vol %, 3.5 to 3.75 vol %, 3.75 to 4 vol %, 4 to 4.25 vol %, 4.25 to 4.5 vol %, 4.5 to 4.75 vol %, 4.75 to 5 vol %, 5 to 6 vol %, 6 to 7 vol %, 7 to 8 vol %, 8 to 9 vol %, 9 to 10 vol %, and 10 to 15 vol %.

In embodiments, the oxygen concentration in the product (B3) includes one or more concentration ranges selected from the group consisting of 0 to 0.01 volume percent of oxygen (vol %), 0.01 to 0.02 vol %, 0.02 to 0.03 vol %, 0.03 to 0.04 vol %, 0.04 to 0.05 vol %, 0.05 to 0.06 vol %, 0.06 to 0.07 vol %, 0.07 to 0.08 vol %, 0.08 to 0.09 vol %, 0.09 to 0.1 vol %, 0.1 to 0.15 vol %, 0.15 to 0.2 vol %, 0.2 to 0.25 vol %, 0.25 to 0.3 vol %, 0.3 to 0.35 vol %, 0.35 to 0.4 vol %, 0.4 to 0.45 vol %, 0.45 to 0.5 vol %, 0.5 to 0.55 vol %, 0.55 to 0.6 vol %, 0.6 to 0.65 vol %, 0.65 to 0.7 vol %, 0.7 to 0.75 vol %, 0.75 to 0.8 vol %, 0.8 to 0.85 vol %, 0.85 to 0.9 vol %, 0.9 to 0.95 vol %, 0.95 to 1 vol %, 1 to 1.5 vol %, 1.5 to 2 vol %, 2 to 2.5 vol %, 2.5 to 3 vol %, 3 to 3.5 vol %, 3.5 to 4 vol %, 4 to 4.5 vol %, and 4.5 to 5 vol %.

In embodiments, said pre-processed biogas (A3) or an acid-laden biogas (50) is then supplied to said biogas acid removal system (100) to remove acid therefrom then supplied to a post-processing system (B) comprising for further processing into a product (B3). In embodiments, said pre-processed biogas (A3) or an acid-laden biogas (50) is then supplied to said biogas acid removal system (100) to remove acid therefrom then supplied to a post-processing system (B) comprising water removal for further processing. In embodiments, the water that is removed may be condensed and may be acidic and may require additional processing such as a neutralization process. In embodiments, the neutralization process comprises a chemical reaction process whereby said acid condensate is mixed with a base. In embodiments, the neutralization process results in there being no excess of hydrogen or hydroxide ions present in the acidic condensate removed in the water removal process.

FIG. 4 describes the following halogenated volatile organic compound removal process, comprising:

a halogenated volatile organic compound removal system (A) configured to accept said source of biogas (A0) comprising methane, oxygen, and a halogenated volatile organic compound, and within said halogenated volatile organic compound removal system (A) subjecting said source of biogas (A0) to a combustion process to produce a pre-processed biogas (A3), said pre-processed biogas (A3) comprises a reduced amount of said oxygen, and a reduced amount of said halogenated volatile organic compound relative to said source of biogas (A0), wherein the halogen portion of said halogenated volatile organic compound is disassociated into said halogen by said combustion process, wherein said halogen combines with water vapor within said pre-processed biogas (A3) to produce an acid, said pre-processed biogas (A3) comprises said acid and is evacuated from said pre-processing system (A) and supplied to a biogas acid removal system (100);

said biogas acid removal system (100) accepts said pre-processed gas (A3) from said pre-processing system (A), said biogas acid removal system (100) removes said acid from said pre-processed biogas (A3) to produce an acid-depleted biogas (55), said acid-depleted biogas (55) is evacuated from said biogas acid removal system (100) and supplied to a post-processing system (B), wherein said acid-depleted biogas (55) comprises a reduced amount of said acid relative to said pre-processed biogas (A3); and said post-processing system (B) accepts said acid-depleted biogas (55) from said biogas acid removal system (100) and processes said acid-depleted biogas (55) within said post-processing system (B) to produce said product (B3).

FIG. 5

Figure 5:
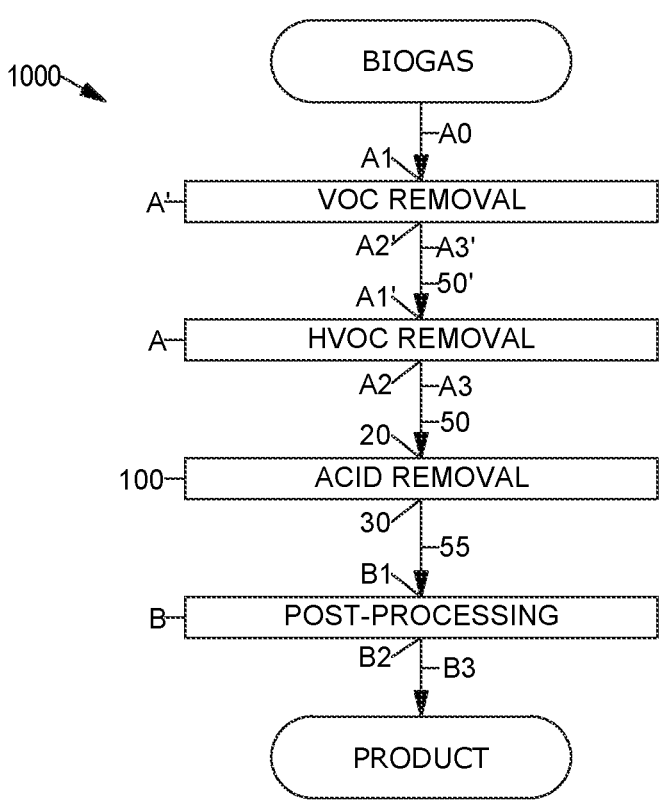
FIG. 5 describes a two-stage volatile organic compound removal process.

FIG. 5 describes a two-stage volatile organic compound removal process, comprising:

a volatile organic compound removal system (A') configured to accept said source of biogas (A0) comprising methane and a volatile organic compound, and process said biogas (A0) within said volatile organic compound removal system (A') to produce a pre-processed biogas (A3'), said pre-processed biogas (A3') is evacuated from said volatile organic compound removal system (A') and supplied to a halogenated volatile organic compound removal system (A), said pre-processed biogas (A3') comprises a reduced amount of said volatile organic compound relative to said source of biogas (A0); wherein said a volatile organic compounds are subjected to an adsorption process within said a volatile organic compound removal system (A') to produce said pre-processed biogas (A3');

said halogenated volatile organic compound removal system (A') is configured to accept said source of pre-processed biogas (A3') comprising methane, oxygen, and a halogenated volatile organic compound, and within said halogenated volatile organic compound removal system (A) subjecting said pre-processed biogas (A3') to a combustion process to produce a secondary pre-processed biogas (A3), said secondary pre-processed biogas (A3) comprises a reduced amount of said oxygen, and a reduced amount of said halogenated volatile organic compound relative to said pre-processed biogas (A3'), wherein the halogen portion of said halogenated volatile organic compound is disassociated into said halogen by said combustion process, wherein said halogen combines with water vapor within said secondary pre-processed biogas (A3) to produce an acid, said secondary pre-processed biogas (A3) comprises said acid and is evacuated from said pre-processing system (A) and supplied to a biogas acid removal system (100);

said biogas acid removal system (100) accepts said pre-processed gas (A3) from said pre-processing system (A), said biogas acid removal system (100) removes said acid from said pre-processed biogas (A3) to produce an acid-depleted biogas (55), said acid-depleted biogas (55) is evacuated from said biogas acid removal system (100) and supplied to a post-processing system (B), wherein said acid-depleted biogas (55) comprises a reduced amount of said acid relative to said pre-processed biogas (A3); and said post-processing system (B) accepts said acid-depleted biogas (55) from said biogas acid removal system (100) and processes said acid-depleted biogas (55) within said post-processing system (B) to produce said product (B3).

In embodiments, the volatile organic compound removal system (A') also removes halogenated volatile organic compounds. In embodiments, the volatile organic compound removal system (A') comprises a vacuum pressure swing adsorption process. In embodiments, the volatile organic compound removal system (A') comprises a pressure swing adsorption process. In embodiments, the volatile organic compound removal system (A') comprises a temperature swing adsorption process.

It will be appreciated that the foregoing examples, given for purposes of illustration, are not to be construed as limiting the scope of this disclosure. Although only a few exemplary embodiments of this disclosure have been described in detail above, those skilled in the art will readily appreciate that many variation of the theme are possible in the exemplary embodiments without materially departing from the novel teachings and advantages of this disclosure.

Accordingly, all such modifications are intended to be included within the scope of this disclosure that is defined in the following claims and all equivalents thereto. Further, it is recognized that many embodiments may be conceived in the design of a given system that do not achieve all of the advantages of some embodiments, yet the absence of a particular advantage shall not be construed to necessarily mean that such an embodiment is outside the scope of the present disclosure.

Thus, specific systems and methods of an automated fluidized bed level and density measurement system have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the foregoing text sets forth a detailed description of numerous different embodiments of the disclosure, it should be understood that the scope of the disclosure is defined by the words of the claims set forth at the end of this patent. The detailed description is to be construed as exemplary only and does not describe every possible embodiment of the disclosure because describing every possible embodiment would be impractical, if not impossible. Numerous alternative embodiments could be implemented, using either current technology or technology developed after the filing date of this patent, which would still fall within the scope of the claims defining the disclosure.

Thus, many modifications and variations may be made in the techniques and structures described and illustrated herein without departing from the spirit and scope of the present disclosure. Accordingly, it should be understood that the methods and apparatus described herein are illustrative only and are not limiting upon the scope of the disclosure.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

What is claimed is:

1. A method to produce a water-depleted gas, comprising:
providing a pre-processing system configured to accept a gas comprising at least methane, oxygen, and a halogenated volatile organic compound, wherein said gas is a source of biogas, and to subject said gas to a combustion process within said pre-processing system to produce a pre-processed gas; wherein said pre-processed gas comprises carbon dioxide, water vapor, a reduced amount of said oxygen, and a reduced amount of said halogenated volatile organic compound relative to said gas, wherein a halogen portion of said halogenated volatile organic compound is dissociated into said halogen by said combustion process, wherein said halogen combines with said water vapor within said pre-processed gas to produce an acid, wherein said pre-processed gas comprises at least said acid and said water vapor, and said pre-processing system is further configured to evacuate said pre-processed gas from said pre-processing system and supply said pre-processed gas to an acid removal system;
providing said acid removal system comprising an acid removal material, said acid removal system is configured to accept said pre-processed gas and contact said pre-processed gas with said acid removal material within said acid removal system to remove at least a portion of said acid from said pre-processed gas to produce an acid-depleted gas, said acid-depleted gas comprises a reduced amount of said acid relative to said pre-processed gas; wherein said acid removal system does not comprise a liquid caustic scrubber; wherein said acid removal system is further configured to evacuate said acid-depleted gas from said acid removal system and supply said acid-depleted gas to a temperature swing adsorption water removal process;
providing said temperature swing adsorption water removal process configured to accept said acid-depleted gas from said acid removal system and remove at least a portion of said water vapor from said acid-depleted gas to produce said water-depleted gas, wherein said water-depleted gas comprises a reduced amount of said water vapor relative to said acid-depleted gas;
supplying said gas to said pre-processing system, and within said pre-processing system, subjecting said gas to said combustion process to produce said pre-processed gas, said pre-processed gas comprises an increased amount of carbon dioxide, an increased amount of water vapor, a reduced amount of said oxygen, and a reduced amount of said halogenated volatile organic compound relative to said gas, wherein said halogen portion of said halogenated volatile organic compound is dissociated into said halogen by said combustion process, wherein said halogen combines with said water vapor within said pre-processed gas to produce said acid;
supplying said pre-processed gas to said acid removal system, wherein within said acid removal system said pre-processed gas is contacted with said acid removal material to remove at least a portion of said acid from said pre-processed gas to produce said acid-depleted gas, wherein said acid-depleted gas comprises a reduced amount of said acid relative to said pre-processed gas; and supplying said acid-depleted gas to said temperature swing adsorption water removal process to remove at least a portion of said water vapor from said acid-depleted gas to produce said water-depleted gas, said water-depleted gas comprises a reduced amount of said water vapor relative to said acid-depleted gas, said increased amount of carbon dioxide, said reduced amount of said oxygen, and said reduced amount of said halogenated volatile organic compound, wherein said at least a portion of said water is removed from said acid-depleted gas without supplying said acid-depleted gas to a carbon dioxide removal process.

2. The method according to claim 1, wherein:

said acid removal system comprises a vessel, wherein said vessel comprises an interior with said acid removal material positioned within said interior; and said method further comprises:

supplying said pre-processed gas to said vessel, wherein said pre-processed gas contacts said acid removal material positioned within said interior of said vessel to produce said acid-depleted gas.

3. The method according to claim 1, wherein:

said acid removal system comprises a plurality of vessels, wherein each of said plurality of vessels comprise an interior with said acid removal material positioned within said interior; said plurality of vessels comprises a first vessel and a second vessel; said first vessel is configured to accept said pre-processed gas and to remove a first portion of said acid therefrom to produce an intermediate acid-depleted gas by contacting said pre-processed gas with said acid removal material within said first vessel; said second vessel is configured to accept said intermediate acid-depleted gas from said first vessel and to remove a second portion of said acid therefrom to produce said acid-depleted gas by contacting said intermediate acid-depleted gas with said acid removal material included within said second vessel; and said method further comprises:

supplying said pre-processed gas to said first vessel to remove said first portion of said acid therefrom to produce said intermediate acid-depleted gas by contacting said pre-processed gas with said acid removal material within said first vessel; and supplying said intermediate acid-depleted gas from said first vessel to said second vessel to remove said second portion of said acid therefrom to produce said acid-depleted gas by contacting said intermediate acid-depleted gas with said acid removal material included within said second vessel;

wherein:

said intermediate acid-depleted gas comprises a reduced amount of acid relative to said pre-processed gas;

said acid-depleted gas comprises a reduced amount of acid relative to said intermediate acid-depleted gas; and wherein:

said acid removal material within said second vessel comprises a type of acid removal material that is either the same or different from said acid removal material within said first vessel.

4. The method according to claim 1, wherein:

prior to supplying said gas to said pre-processing system, processing at least a portion of said gas in one or more processing systems selected from the group consisting of pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

5. The method according to claim 1, further comprising:

providing a post-processing system configured to accept said water-depleted gas from said temperature swing adsorption water removal process and process said water-depleted gas in said post-processing system to produce a product; and supplying said water-depleted gas from said temperature swing adsorption water removal process to said post-processing system, and within said post-processing system, processing said depleted gas to produce said product.

6. The method according to claim 5, wherein:

said post-processing system comprises one or more processing systems selected from the group consisting of pre-pressurization with at least one blower, a hydrogen sulfide removal process, biogas chilling, biogas pressurization, a volatile organic compound removal process, a carbon dioxide removal process, a catalytic oxygen reduction process, an oxygen removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, processing in a fuel cell, and a bioreactor including microorganisms.

7. The method according to claim 1, further comprising:

producing a product from at least a portion of said water-depleted gas, said product comprises one or more products selected from the group consisting of renewable natural gas, a chemical, dimethyl ether, ethanol, Fischer-Tropsch product, hydrogen, methanol, mixed alcohols, an alcohol, 1-butanol, 2-butanol, jet fuel, gasoline, a liquid fuel, diesel, and power.

8. The method according to claim 1, further comprising:

condensing said water vapor removed from said water-depleted gas into liquid water comprising an acid; and neutralizing said acid within said liquid water with a base.

9. The method according to claim 1, wherein at least a portion of said biogas is produced in one or more selected from the group consisting of: an anaerobic digester, a landfill, and a waste water treatment facility; and/or wherein said biogas further comprises an additional acid.

10. The method according to claim 1, wherein:

said acid removal material comprises one or more materials selected from the group consisting of an adsorbent, activated alumina, activated carbon, alumina, caustic, carbon, carbon nanotubes, catalyst, ceramic material, chitosan, chitin, clay, a dry scrubbing agent, an engineered reactant, iron sponge, an ion-exchange resin, media, molecular sieve, a polymeric adsorbent, a reactant, a scavenger, silica gel, a base, a neutralizing agent, a pH buffer, and a zeolite.

11. The method according to claim 1, wherein:

said acid removal material comprises promoted alumina.

12. The method according to claim 1, wherein:

said acid removal material comprises metal promoted alumina.

13. The method according to claim 1, wherein:

said combustion process occurs in the presence of a catalyst.

14. The method according to claim 1, wherein:

said gas comprises said oxygen at a concentration less than 15 percent by volume; and said water-depleted gas comprises said oxygen at a concentration less than 5 percent by volume.

15. A method to produce a water-depleted gas, comprising:

providing a gas comprising carbon dioxide, methane, and a halogenated volatile organic compound, wherein said gas is a processed source of biogas and/or includes biogas;

removing at least a portion of said carbon dioxide from said gas to produce a carbon dioxide depleted gas, wherein said carbon dioxide depleted gas comprises a reduced amount of said carbon dioxide relative to said gas;

removing at least a portion of said halogenated volatile organic compound from said carbon dioxide depleted gas to produce a halogenated volatile organic compound depleted gas by subjecting said carbon dioxide depleted gas to a combustion process and/or contacting said carbon dioxide depleted gas with a catalyst, wherein said halogenated volatile organic compound depleted gas comprises a reduced amount of said halogenated volatile organic compound relative to said carbon dioxide depleted gas, wherein said halogenated volatile organic compound depleted gas comprises an acid and water vapor;

contacting at least a portion of said halogenated volatile organic compound depleted gas with an acid removal material to remove at least a portion of said acid from said halogenated volatile organic compound depleted gas to produce an acid-depleted gas, wherein said acid-depleted gas comprises a reduced amount of said acid relative to said halogenated volatile organic compound depleted gas; wherein said acid removal material comprises one or more materials selected from the group consisting of an adsorbent, activated alumina, activated carbon, alumina, carbon, carbon nanotubes, catalyst, ceramic material, chitosan, chitin, clay, a dry scrubbing agent, an engineered reactant, iron sponge, an ion-exchange resin, molecular sieve, a polymeric adsorbent, promoted alumina, a reactant, a scavenger, silica gel, a base, a neutralizing agent, a pH buffer, and a zeolite; and removing at least a portion of said water vapor from said acid-depleted gas to produce said water-depleted gas, wherein said water-depleted gas comprises a reduced amount of said water vapor relative to said acid-depleted gas.

16. The method according to claim 15, comprising:

removing said halogenated volatile organic compound from said carbon dioxide depleted gas by subjecting said carbon dioxide depleted gas to a combustion process and/or contacting said carbon dioxide depleted gas with a catalyst.

17. The method according to claim 16, further comprising:

after removing at least a portion of said water vapor from said acid-depleted gas, supplying at least a portion of said water-depleted gas to one or more processing systems selected from the group consisting of chilling, pressurization, a volatile organic compound removal process, a carbon dioxide removal process, a pressure-swing adsorption process, a nitrogen removal process, a temperature swing adsorption process, a membrane separation process, a membrane carbon dioxide removal process, a metal removal process, a mercury removal process, a cryogenic gas separation process, a water-wash gas separation process, a cryogenic distillation process, a distillation process, a hydrogen production process, a partial oxidation process, an autothermal reforming process, a chemical production process, an ethanol production process, an alcohol production process, a liquid fuel production process, a Fischer Tropsch synthesis process, a steam methane reforming process, a catalytic process, an ammonia production process, a fuel cell, and a bioreactor including microorganisms; and/or producing a product from said water-depleted gas, said product comprises one or more products selected from the group consisting of renewable natural gas, a chemical, dimethyl ether, ethanol, Fischer-Tropsch product, hydrogen, methanol, mixed alcohols, an alcohol, 1-butanol, 2-butanol, jet fuel, gasoline, a liquid fuel, diesel, and power.

18. The method according to claim 16, wherein:

said halogenated volatile organic compound depleted gas comprises an increased amount of said acid relative to said carbon dioxide depleted gas; and/or said halogenated volatile organic compound comprises a halogen, and the method comprises removing at least a portion of said halogenated volatile organic compound from said gas by removing at least a portion of said halogen from said halogenated volatile organic compound, wherein said halogen removed from said halogenated volatile organic compound forms said acid, and said acid is supplied to said acid removal material together with said halogenated volatile organic compound depleted gas, to remove said acid therefrom and produce said acid-depleted gas.

19. The method according to claim 15, wherein:

removing at least a portion of said water vapor in a temperature swing adsorption water removal process.

* * * * *